(12) United States Patent
Ma et al.

(10) Patent No.: US 9,964,475 B2
(45) Date of Patent: May 8, 2018

(54) DEVICE AND METHOD USING INFRARED RADIATION TO OBSERVE COAL ROCK FRACTURE DEVELOPMENT PROCESS

(71) Applicant: China University of Mining and Technology, Xuzhou (CN)

(72) Inventors: Liqiang Ma, Xuzhou (CN); Hai Sun, Xuzhou (CN); Yayong Jiang, Xuzhou (CN); Jimeng Liang, Xuzhou (CN); Bin Yu, Xuzhou (CN); Tiejun Kuang, Xuzhou (CN)

(73) Assignee: China University of Mining and Technology, Xuzhou (CN)

( * ) Notice: Subject to any disclaimer, the term of this patent is extended or adjusted under 35 U.S.C. 154(b) by 25 days.

(21) Appl. No.: 15/305,786

(22) PCT Filed: Nov. 19, 2014

(86) PCT No.: PCT/CN2014/091510
§ 371 (c)(1),
(2) Date: Oct. 21, 2016

(87) PCT Pub. No.: WO2015/176508
PCT Pub. Date: Nov. 26, 2015

(65) Prior Publication Data
US 2017/0059462 A1    Mar. 2, 2017

(30) Foreign Application Priority Data
May 22, 2014   (CN) .......................... 2014 1 0220058

(51) Int. Cl.
*G01N 3/08*     (2006.01)
*H04N 5/77*     (2006.01)
(Continued)

(52) U.S. Cl.
CPC ................. *G01N 3/08* (2013.01); *G01J 5/025* (2013.01); *G01J 5/10* (2013.01); *G01N 33/222* (2013.01);
(Continued)

(58) Field of Classification Search
None
See application file for complete search history.

(56) References Cited

U.S. PATENT DOCUMENTS

| | | | | |
|---|---|---|---|---|
| 4,531,403 A | * | 7/1985 | de Korompay | E21B 47/10 73/37 |
| 4,665,984 A | * | 5/1987 | Hayashi | E21B 43/26 166/250.1 |

(Continued)

FOREIGN PATENT DOCUMENTS

| | | |
|---|---|---|
| CN | 103983513 A | 8/2014 |
| JP | 2001324430 A | 11/2001 |

OTHER PUBLICATIONS

International Search Report re PCT/CN2014/091510, dated Feb. 15, 2015, 4 pgs.

(Continued)

*Primary Examiner* — Frederick D Bailey
(74) *Attorney, Agent, or Firm* — Greenberg Traurig, LLP

(57) ABSTRACT

A device and method of using infrared radiation to observe coal rock fracture development processes, for use in experiments to monitor coal rock fracture development using infrared radiation comprises three telescopic box bodies sleeved together. An infrared thermal imager connected to a computer is arranged at the front end of the telescopic box bodies, and a light-blocking plate is installed on a rear end. The distance between a coal rock test block and a lens of the infrared thermal imager can be freely adjusted via the three telescopic box bodies. The telescopic box bodies are (Continued)

installed on a rock press, and a loading test is performed on the coal rock test block.

4 Claims, 3 Drawing Sheets

(51) Int. Cl.
G01N 33/22 (2006.01)
H04N 5/33 (2006.01)
G01J 5/10 (2006.01)
G01J 5/02 (2006.01)
G01J 5/00 (2006.01)

(52) U.S. Cl.
CPC ............... H04N 5/33 (2013.01); H04N 5/77 (2013.01); H04N 5/772 (2013.01); G01J 2005/0077 (2013.01); G01N 2203/0003 (2013.01); G01N 2203/0032 (2013.01); G01N 2203/0067 (2013.01); G01N 2203/0087 (2013.01); G01N 2203/0641 (2013.01); G01N 2203/0694 (2013.01)

(56) References Cited

U.S. PATENT DOCUMENTS

| 6,912,356 | B2* | 6/2005 | Arrison | B28D 1/221 |
| | | | | 175/16 |
| 7,171,328 | B1* | 1/2007 | Walker | G01V 9/005 |
| | | | | 702/130 |
| 2008/0137105 | A1* | 6/2008 | Howard | G01N 25/72 |
| | | | | 356/630 |
| 2011/0239764 | A1* | 10/2011 | Bellin | G01N 29/14 |
| | | | | 73/573 |
| 2012/0200713 | A1* | 8/2012 | Brink | G01H 3/08 |
| | | | | 348/162 |

OTHER PUBLICATIONS

Liu, Peixun et al., "An Experiment on the Infrared Radiation of Surficial Rocks During Deformation", Seismology and Geology, vol. 26, No. 3, p. 503, section 1, p. 504, figure 1 and p. 504, section 2.1, Sep. 30, 2004.

Liu, Liqiang et al., Infrared Measurement System for Rock Deformation Experiement, Seismology and Geology, vol. 26, No. 3, Sep. 30, 2004.

* cited by examiner

DEVICE AND METHOD USING INFRARED RADIATION TO OBSERVE COAL ROCK FRACTURE DEVELOPMENT PROCESS

CROSS REFERENCE TO RELATED APPLICATION

The present application is a 371 U.S. National Stage of International Application No. PCT/CN2014/091510, filed Nov. 19, 2014, which claims the benefit of the earlier filing date of Chinese Patent Application No. 201410220058.7 filed on May 22, 2014, which are each incorporated herein by reference in their entirety.

FIELD OF THE DISCLOSURE

The present disclosure relates to a device and a method using infrared radiation to observe the coal rock fracture development process, and belongs to the field of remote sensing—rock mechanics.

BACKGROUND OF RELATED ART

In recent years, many researchers utilized infrared remote sensing technique to monitor the rock failure process under stress, and made numerous researches on the infrared radiation temperature characteristics in the rock failure process under stress. The research findings indicate the rock has a regular infrared radiation effect in the process from deformation to failure under stress, and there is an infrared anomaly omen before catastrophic failure of rock.

Since the beginning of 1990s, many experts and researchers have set up indoor thermal infrared observation and testing systems to make research on the relationship between rock deformation and temperature change, have accomplished many thermal infrared tests and experiments on the deformation of materials such as rock and coal, and the researches have received extensive attention. However, their observation results had high discreteness, and some of the observation results deviated from the traditional theory. For example, it is believed that the relationship between stress state and temperature change depends on the species of the rock. For example, some rocks exhibit a temperature rise characteristic when they are compressed, some rocks have no temperature change when they are compressed, and other rocks even exhibit a temperature drop characteristic when they are compressed; in addition, the amplitude of temperature change to the rock collapse point is different among different species of rocks. The main reason for such discreteness is that the tester didn't take appropriate measures to minimize the influences of environmental factors and background factors.

A part of the radiation received by a thermal infrared imager comes from the radiation of ambient and background reflection in the air path. The surface temperature of the tested object may change at any time, depending on the geographical location, season, solar radiation, sky radiation, climatic change, and air flow, and existence of any heat source, etc. at the test place. In addition, the surface of the tested object exchanges heat with the ambient medium uninterruptedly by radiation, convection, and conduction, etc. The ambient influences on the temperature of a tested object can be considered mainly in two aspects: environmental factors and background factors. The environmental factors mainly refer to the influences of the natural environment on the tested object, including direct solar radiation, sky radiation, earth background radiation and reflection of other radiations, air temperature change, wind speed, geographical latitude, and nearby landform and topography, etc. Under given geographical latitude, given orientation of the tested object, and given topographical conditions, the major influencing factors include solar radiation intensity, air temperature change, and wind speed, etc.

SUMMARY

Technical Problem

To overcome the drawbacks in the prior art, the present invention provides a device and a method for reducing the error in the monitoring and test of coal rock fracture development with infrared radiation, which are simple and reasonable, scientific in structure, easy to install, and can effectively reduce the influences of environmental factors and background factors, reduce experimental error, and greatly improving test efficiency and data accuracy.

Technical Solution

The device using infrared radiation to observe the coal rock fracture development process provided in the present invention comprises a thermal infrared imager, a computer, and three telescopic box bodies sleeved together. Slide-off preventing plugs are provided at the relatively sliding limit positions on adjacent two box bodies among the box bodies; the first box body and the second box body are composed of four identical rectangular thermal insulating plates respectively; the third box body is composed of four identical rectangular thermal insulating plates and a square thermal insulating plate that seals the opening; a monitoring port is arranged on the square thermal insulating plate, the thermal infrared imager is mounted inside the monitoring port, with the lens of the thermal infrared imager facing the coal rock test block, and the distance between the thermal infrared imager and the coal rock test block can be changed by the sliding of the three telescopic box bodies in relation to each other; the thermal infrared imager is connected to the computer via conductive wires; a light barrier plate is mounted on the rear end face of the first box body, and the light barrier plate is made of the thermal insulating plate and is connected with a side plate of the first box body via a hinge; a round hole through which a plunger of a rock press machine can pass is arranged on the top thermal insulating plate of the first box body, a U-slot through which a workbench of the rock press machine can pass is arranged on the bottom thermal insulating plate of the first box body, and the arc of the U-slot is concentric with the round hole.

A rubber sleeve is fitted around the round hole, one end of the rubber sleeve is glued to the first box body, and the other end of the rubber sleeve is fitted over the plunger of the rock press machine.

Each of the thermal insulating plates is composed of a wood plate in thickness of 5 mm and an aluminum foil coated on the wood plate.

The method using infrared radiation to observe the coal rock fracture development process with the above-mentioned device comprises the following steps:

a. removing a pin on the plunger of the rock press machine, removing the press plate of the rock press machine and lifting the plunger of the rock press machine till the telescopic box bodies can be placed under the plunger, placing the side of the telescopic box bodies at which the light barrier plate exists among the columns of the rock press machine, opening the light barrier plate, and clamping the U-slot to a support pillar of the workbench of the rock press machine;

b. laying the telescopic box bodies level, lowering the plunger of the rock press machine so that the plunger passes through the round hole on the top thermal insulating plate of the first box body, fitting one end of the rubber sleeve on the plunger to baffle incident ambient light;

c. wearing heat insulating gloves, opening the light barrier plate on the first box body, fixing the press plate of the rock press machine with the pin to the plunger of the rock press machine, moving up and down the plunger of the rock press machine, and observing the coupling between the plunger of the rock press machine and the round hole on the top thermal insulating plate of the first box body, to ensure the incident ambient light is blocked there and the plunger can move up and down freely;

d. opening the light barrier plate on the first box body, and loading a coal rock test block onto the workbench of the rock press machine from the rear side of the first box body;

e. adjusting the telescopic box bodies to level state, starting the thermal infrared imager extending into the monitoring port on the third box body, and activating a video recording function of the thermal infrared imager;

f. starting the rock press machine to apply load to the coal rock test block according to the preset pressure, till the coal rock test block collapses; thus, the load test of the coal rock test block is completed;

g. stopping the loading, closing the video recording function of the thermal infrared imager, converting the video content of the entire load bearing process of the coal rock test block into digital signals, and transmitting the digital signals to the computer for analysis and processing;

h. opening the light barrier plate, wearing heat insulating gloves and clearing the broken coal rock test block on the workbench of the rock press machine;

i. repeating the above steps to perform load test of the next coal rock test block.

Beneficial Effects

With the technical solution described above, in the present invention, telescopic box bodies made of thick wood plates coated with an aluminum foil are used and mounted on a rock press machine to perform load test of coal rock test blocks. Thus, the influences of testing personnel, solar radiation, temperature fluctuation, air flow, and heat sources on the infrared radiation information in the coal rock fracture development process are reduced. In addition, utilizing three telescopic box bodies, the distance between the coal rock test block and the lens of the thermal infrared imager can be adjusted. The method is simple reasonable, convenient and scientific, can greatly improve test efficiency and test data accuracy, and is of guiding significance for infrared radiation monitoring and tests in the load bearing process of coal rock, can effectively reduce the influences of environmental factors and background factors on the authenticity of the test data in the infrared radiation monitoring and tests of coal rock fracture development, and is especially applicable to infrared radiation monitoring and tests of coal rock fracture development. The device and the method are simple, easy to use, can attain a good test result, and have extensive practicability in the art.

DETAILED DESCRIPTION

Figure 1:
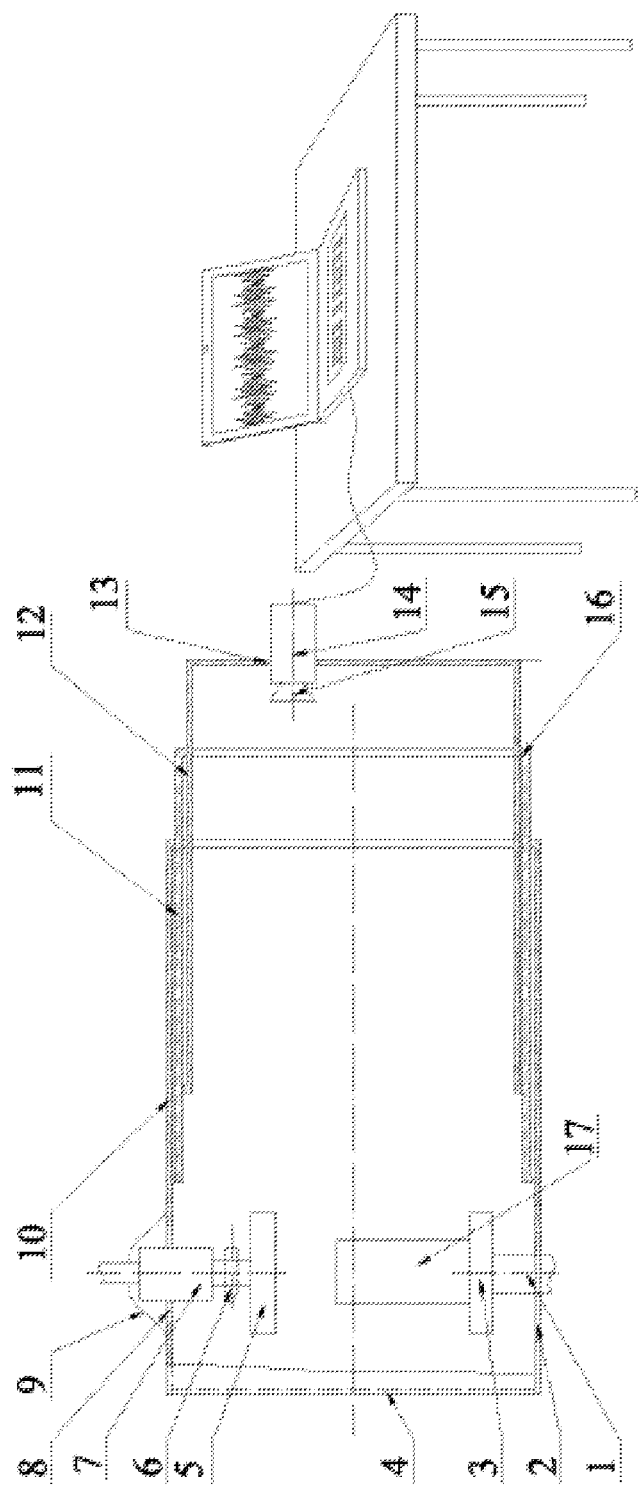
FIG. 1 is a front view of the structure of the device according to the present invention.
Figure 2:
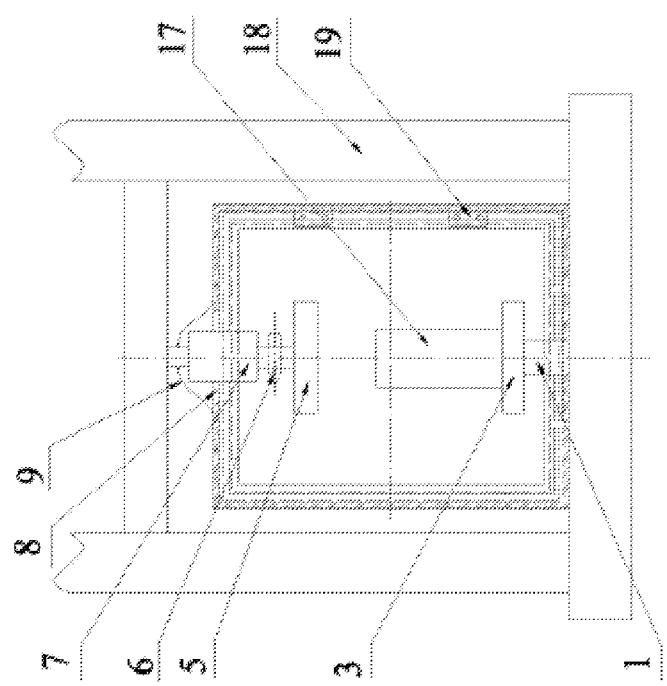
FIG. 2 is a side sectional view of the structure of the device according to the present invention.

Hereunder the present invention will be detailed in embodiments with reference to the accompanying drawings:

As shown in FIG. 1, the device using infrared radiation to observe the coal rock fracture development process in the present invention mainly comprises three telescopic box bodies sleeved together, a thermal infrared imager 14, and a computer, wherein, slide-off preventing plugs 16 are provided at relatively sliding limit positions on adjacent box bodies among the box bodies. The first box body 10 and the second box body 11 are composed of four identical rectangular thermal insulating plates nailed together respectively. The third box body 12 is composed of four identical rectangular thermal insulating plates and a square thermal insulating plate that seals the opening, which are nailed together. Each of the thermal insulating plates is composed of a wood plate in thickness of 5 mm and an aluminum foil coated on the wood plate.

A monitoring port 13 is arranged on the square thermal insulating plate, the thermal infrared imager 14 is mounted inside the monitoring port 13, with the lens 15 of the thermal infrared imager 14 facing the coal rock test block 17, and the dimensions of the monitoring port 13 are determined according to the dimensions of the lens 15 of the thermal infrared imager 14. The distance between the thermal infrared imager 14 and the coal rock test block 17 can be changed by the sliding of the three telescopic box bodies in relation to each other. The thermal infrared imager 14 is connected to the computer via conductive wires. A light barrier plate 4 is mounted on the rear end face of the first box body 10, and the light barrier plate 4 is made of the thermal insulating plate described above and is connected with a side plate of the first box body 10 via a hinge 19. The dimensions of the light barrier plate 4 are determined according to the dimensions of the box bodies, so that it can block the incident ambient light. A round hole 8 through which a plunger 7 of a rock press machine can pass is arranged on the top thermal insulating plate of the first box body 10, and the size of the round hole 8 is determined according to the diameter of the plunger 7 of the rock press machine.

Figure 3:
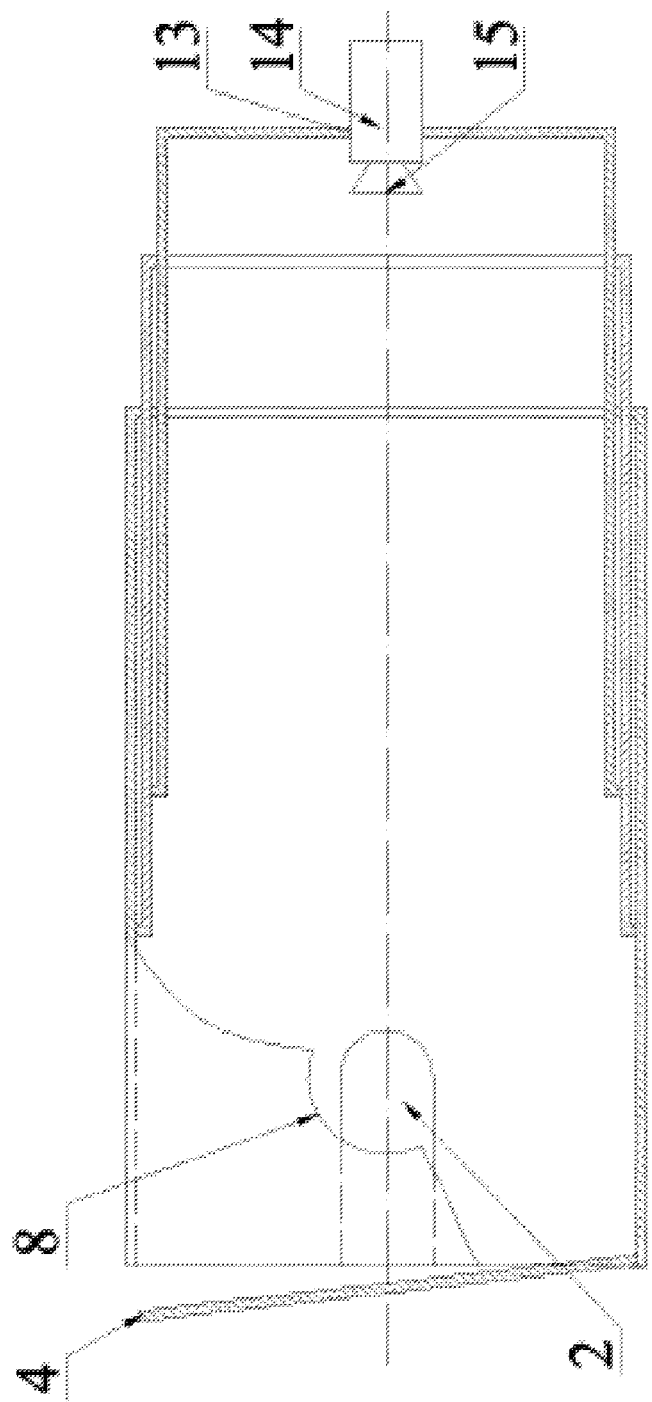
FIG. 3 is a top view of the structure of the device according to the present invention.

A rubber sleeve 9 is fixed around the round hole 8, one end of the rubber sleeve 9 is glued to the periphery of the round hole 8 on the top thermal insulating plate of the first box body 10, and the other end of the rubber sleeve 9 is fitted over the plunger 7 of the rock press machine in a way that the incident ambient light can be blocked there and the plunger 7 of the press machine can move up and down freely, so as to adapt to coal rock test blocks 17 in different sizes. A press plate 5 of the rock press machine is fixedly connected to the plunger 7 of the rock press machine via a pin 6. A U-slot 2 through which a workbench 3 of the rock press machine can pass is arranged on the bottom thermal insulating plate of the first box body 10, as shown in FIG. 3. The dimensions of the U-slot 2 are determined according to the dimensions of a support pillar 1 of the workbench of the rock press machine, and the arc of the U-slot 2 is concentric with the round hole 8 on the top thermal insulating plate of the first box body 10.

The method using infrared radiation to observe the coal rock fracture development process in the present invention comprises the following steps:

Removing the pin 6 on the plunger 7 of the rock press machine, removing the press plate 5 of the rock press machine and lifting the plunger 7 of the rock press machine till the telescopic box bodies can be placed under the plunger 7, placing the side of the telescopic box bodies at which the light barrier plate 4 exists among the columns 18 of the rock press machine, opening the light barrier plate 4, and clamping the U-slot 2 to the support pillar 1 of the workbench of the rock press machine.

Laying the telescopic box bodies level, lowering the plunger 7 of the rock press machine so that the plunger 7 of the rock press machine passes through the round hole 8 on the top thermal insulating plate of the first box body 10, fitting one end of the rubber sleeve 9 on the plunger 7 to baffle incident ambient light.

Wearing heat insulating gloves, opening the light barrier plate 4 on the first box body 10, fixing the press plate 5 of the rock press machine with the pin 6 to the plunger 7 of the rock press machine, moving up and down the plunger 7 of the rock press machine, and observing the coupling between the plunger 7 of the rock press machine and the round hole 8 on the top thermal insulating plate of the first box body 10, to ensure the incident ambient light is blocked there and the plunger 7 can move up and down freely.

Opening the light barrier plate 4 on the first box body 10, and loading a coal rock test block 17 onto the workbench 3 of the rock press machine from the rear side of the first box body 10.

Adjusting the telescopic box bodies to level state, extending the lens 15 of the thermal infrared imager into the monitoring port 13 on the third box body 12, starting the thermal infrared imager 14 extending into the monitoring port 13 on the third box body 12, and activating a video recording function of the thermal infrared imager 14.

Starting the rock press machine to apply load to the coal rock test block 17 according to the preset pressure, till the coal rock test block 17 collapses; thus, the load test of the coal rock test block 17 is completed.

Stopping the loading, closing the video recording function of the thermal infrared imager 14, converting the video content of the entire load bearing process of the coal rock test block 17 recorded by the thermal infrared imager 14 into digital signals, and transmitting the digital signals to the computer for analysis and processing.

Opening the light barrier plate 4, wearing heat insulating gloves and clearing the broken coal rock test block 17 on the workbench 3 of the rock press machine.

Repeating the above steps to perform load test of the next coal rock test block 17, and so on, till the load test of all coal rock test blocks 17 is completed.

In the figures: 1—support pillar of workbench of rock press machine, 2—U-slot, 3—workbench of rock press machine, 4—light barrier plate, 5—press plate of rock press machine, 6—pin, 7—plunger of rock press machine, 8—round hole, 9—rubber sleeve, 10—first box body, 11—second box body, 12—third box body, 13—monitoring port, 14—thermal infrared imager, 15—lens of thermal infrared imager, 16—slide-off preventing plug, 17—coal rock test block, 18—column of rock press machine, 19—hinge.

We claim:

1. A device using infrared radiation to observe the coal rock fracture development process, comprising a thermal infrared imager and a computer, wherein, the device further comprises:

three telescopic box bodies sleeved together, with slide-off preventing plugs provided at the relatively sliding limit positions on adjacent two box bodies among the box bodies;

the first box body and the second box body are composed of four identical rectangular thermal insulating plates respectively, and the third box body is composed of four identical rectangular thermal insulating plates and a square thermal insulating plate that seals the opening;

a monitoring port is arranged on the square thermal insulating plate, the thermal infrared imager is mounted inside the monitoring port, with the lens of the thermal infrared imager facing a coal rock test block, and the distance between the thermal infrared imager and the coal rock test block can be changed by the sliding of the three telescopic box bodies in relation to each other;

the thermal infrared imager is connected to the computer via conductive wires;

a light barrier plate is mounted on the rear end face of the first box body, and the light barrier plate is made of the thermal insulating plate and is connected with a side plate of the first box body via a hinge;

a round hole through which a plunger of a rock press machine can pass is arranged on the top thermal insulating plate of the first box body, a U-slot through which a support pillar of a workbench of the rock press machine can pass is arranged on the bottom thermal insulating plate of the first box body, and the arc of the U-slot is concentric with the round hole.

2. The device infrared radiation to observe the coal rock fracture development process according to claim 1, wherein: a rubber sleeve is fitted around the round hole, one end of the rubber sleeve is glued to the first box body, and the other end of the rubber sleeve is fitted over the plunger of the rock press machine.

3. The device infrared radiation to observe the coal rock fracture development process according to claim 1, wherein: each of the thermal insulating plates is composed of a wood plate in thickness of 5 mm and an aluminum foil coated on the wood plate.

4. A method using infrared radiation to observe the coal rock fracture development process with the device according to claim 1, comprising the following steps:

a. removing a pin on the plunger of the rock press machine, removing a press plate of the rock press machine and lifting the plunger of the rock press machine till the telescopic box bodies can be placed under the plunger, placing the side of the telescopic box bodies at which the light barrier plate exists among columns of the rock press machine, opening the light barrier plate, and clamping the U-slot to the support pillar of the workbench of the rock press machine;

b. laying the telescopic box bodies level, lowering the plunger of the rock press machine so that the plunger passes through the round hole on the top thermal insulating plate of the first box body, fitting one end of the rubber sleeve on the plunger of the rock press machine to baffle incident ambient light;

c. wearing heat insulating gloves, opening the light barrier plate on the first box body, fixing the press plate of the rock press machine with the pin to the plunger of the rock press machine, moving up and down the plunger of the rock press machine, and observing the coupling between the plunger of the rock press machine and the round hole on the top thermal insulating plate of the first box body, to ensure the incident ambient light is blocked there and the plunger can move up and down freely;

d. opening the light barrier plate on the first box body, and loading a coal rock test block onto the workbench of the rock press machine from the rear side of the first box body;

e. adjusting the telescopic box bodies to level state, starting the thermal infrared imager extending into the monitoring port on the third box body, and activating a video recording function of the thermal infrared imager;

f. starting the rock press machine to apply load to the coal rock test block according to the preset pressure, till the coal rock test block collapses; thus, the load test of the coal rock test block is completed;

g. stopping the loading, closing the video recording function of the thermal infrared imager, converting the video content of the entire load bearing process of the coal rock test block recorded by the thermal infrared imager into digital signals, and transmitting the digital signals to the computer for analysis and processing;

h. opening the light barrier plate, wearing heat insulating gloves and clearing the broken coal rock test block on the workbench of the rock press machine;

i. repeating the above steps to perform load test of the next coal rock test block.

\* \* \* \* \*